(12) United States Patent
Brown et al.

(10) Patent No.: US 11,254,656 B2
(45) Date of Patent: Feb. 22, 2022

(54) MUSCARINIC AGONISTS

(71) Applicant: Heptares Therapeutics Limited, Cambridge (GB)

(72) Inventors: Giles Albert Brown, Cambridge (GB); Julie Elaine Cansfield, Cambridge (GB); Mark Pickworth, Cambridge (GB); Benjamin Gerald Tehan, Cambridge (GB); Barry John Teobald, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

(21) Appl. No.: 16/942,167

(22) Filed: Jul. 29, 2020

(65) Prior Publication Data

US 2020/0354339 A1    Nov. 12, 2020

Related U.S. Application Data

(63) Continuation of application No. 15/749,957, filed as application No. PCT/GB2016/052385 on Aug. 3, 2016, now Pat. No. 10,738,029.

(30) Foreign Application Priority Data

Aug. 3, 2015   (GB) ..................... 1513743

(51) Int. Cl.
*C07D 401/14*    (2006.01)
*A61P 25/28*    (2006.01)
*A61P 25/18*    (2006.01)

(52) U.S. Cl.
CPC ............ *C07D 401/14* (2013.01); *A61P 25/18* (2018.01); *A61P 25/28* (2018.01)

(58) Field of Classification Search
CPC .................................................. C07D 401/14
USPC ................................................... 514/210.02
See application file for complete search history.

(56) References Cited

U.S. PATENT DOCUMENTS 9,266,857 B2    2/2016 Brown et al.
10,738,029 B2   8/2020 Brown et al.

FOREIGN PATENT DOCUMENTS

WO    2007/100670 A1    9/2007
WO    2013/072705 A1    5/2013
WO    2014/045031 A1    3/2014
WO    2015/118342 A1    8/2015
WO    2016/147011 A1    9/2016

OTHER PUBLICATIONS

Conn (Trends in Pharmacological Sciences, 2009, 30(3), 148-155).*
Fisher, J. Neurochem. (2012) 120 (Suppl. 1), 22-33.*
Jorden, ZCommunications, Dec. 20, 2015, pp. 1-4.*
Bradley, Neuropharmacology 58 (2010) 365-373.*
Chung (BMB reports 2009; 42(8): 467-474.*
Hasselmo Neuropsychopharmacology Reviews (2011) 36, 52-73.*
Tietje CNS Neuroscience & Therapeutics 14 (2008) 65-82.*
U.S. Appl. No. 15/749,957, filed Feb. 2, 2018, U.S. Pat. No. 10,738,029, Issued.
Dorwald, Side Reactions in Organic Synthesis, A Guide to Successful Synthesis Design. Wiley-VCH Verlag GmbH & Co. KGaA. pp. 1-16, 40-41, 279-308, (2005).
Venkatesh et al., Role of the development scientist in compound lead selection and optimization. J Pharm Sci. 2000;89(2):145-154.
Great Britain Search Report for Application No. GB1513743.3, dated May 11, 2016.
International Search Report and Written Opinion for Application No. PCT/GB2016/052385, dated Oct. 26, 2016.

\* cited by examiner

*Primary Examiner* — Nizal S Chandrakumar
(74) *Attorney, Agent, or Firm* — McCarter & English, LLP; Steven G. Davis; Mei Bai

(57) ABSTRACT

This invention relates to compounds that are agonists of the muscarinic $M_1$ receptor and/or $M_4$ receptor and which are useful in the treatment of muscarinic $M_1/M_4$ receptor mediated diseases. Also provided are pharmaceutical compositions containing the compounds and the therapeutic uses of the compounds. Compounds include those according to formula 1

(1)

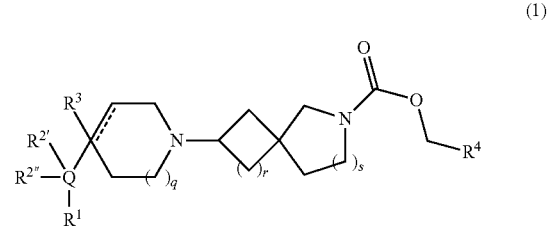

or a salt thereof, wherein q, r, s, Q, $R^1$, $R^{2\dagger}$, $R^{2\prime\prime}$, $R^3$ and $R^4$ are as defined herein.

10 Claims, No Drawings

MUSCARINIC AGONISTS

This application is a continuation of U.S. patent application Ser. No. 15/749,957, filed Feb. 2, 2018, which is a 371 U.S. national phase of International Patent Application No.: PCT/GB2016/052385, filed Aug. 3, 2016, which claims priority to GB Application No.: 1513743.3, filed Aug. 3, 2015, all of which are incorporated herein by reference in their entirety.

This invention relates to compounds that are agonists of the muscarinic $M_1$ receptor and/or $M_4$ receptor and which are useful in the treatment of muscarinic $M_1/M_4$ receptor mediated diseases. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which also has cognitive impairment as an important component of the clinical picture, mAChR density is reduced in the pre-frontal cortex, hippocampus and caudate putamen of schizophrenic subjects (Dean et al., 2002 *Mol Psychiatry*). Furthermore, in animal models, blockade or damage to central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting adverse events resulting from stimulation of peripheral $M_2$ and $M_3$ mAChRs including disturbed gastrointestinal motility, bradycardia, nausea and vomiting (www.drugs.com/pro/donepezil.html; www.drugs.com/pro/rivastigmine.html).

Further discovery efforts have targeted the identification of direct $M_1$ mAChR agonists with the aim of inducing selective improvements in cognitive function with a favourable adverse effect profile. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain pathologies: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidgenic and amyloidgenic. Cleavage of APP by γ-secretase is common to both pathways, but in the former APP is cleaved by an α-secretase to yield soluble APPα. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). The mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Preclinical studies have suggested that mAChR agonists display an atypical antipsychotic-like profile in a range of pre-clinical paradigms. The mAChR agonist, xanomeline, reverses a number of dopamine mediated behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addiction. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models.

Muscarinic receptors are also involved in the control of movement and potentially represent novel treatments for movement disorders such as Parkinson's disease, ADHD, Huntingdon's disease, tourette's syndrome and other syndromes associated with dopaminergic dysfunction as an underlying pathogenetic factor driving disease.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase I study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic adverse events, including nausea, gastrointestinal pain, diahorrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage; however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

The Invention

The present invention provides compounds having activity as muscarinic $M_1$ and/or $M_4$ receptor agonists. More particularly, the invention provides compounds that exhibit selectivity for the $M_1$ receptor and/or the $M_4$ receptor relative to the $M_2$ and $M_3$ receptor subtypes.

Accordingly, in one embodiment (Embodiment 1.1), the invention provides a compound of the formula (1):

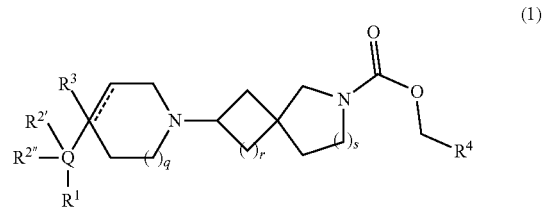

or a salt thereof, wherein
q is 0, 1 or 2;
r is 1 or 2;
s is 0 or 1 where the total of r and s is 1 or 2;
Q is a four membered ring containing 0 or 1 nitrogen atoms;
$R^1$ is selected from hydrogen; fluorine; chlorine; bromine; cyano; oxo; hydroxy; $OR^5$; $NR^5R^6$; $COR^5$; $COOR^5$; $OCOR^5$; $NRCOR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;
$R^{2'}$ and $R^{2''}$ are independently selected from hydrogen; fluorine; chlorine; bromine; cyano; hydroxy; methoxy; $OR^5$; $NR^5R^6$; $COR^5$; $COOR^5$; $OCOR^5$; $NRCOR^5$; $CONR^5R^6$; $NR^7CONR^5R^6$; $NR^7COR^5$; $OCONR^5R^6$; $SR^5$; $SOR^5$ and $SO_2R^5$; a $C_{1-6}$ non-aromatic hydrocarbon group; or $R^1$ and $R^{2'}$ can be joined together to form a 4-7 membered fused ring;
$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;
$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^5$, $R^6$ and $R^7$ are the same or different and each is independently selected from hydrogen, a non-aromatic $C_{1-4}$ hydrocarbon group optionally substituted with one or more fluorine atoms; or a group of formula $CH_2N(R^a)COOR^b$;
$R^a$ is selected from hydrogen and a non-aromatic $C_{1-4}$ hydrocarbon group;
$R^b$ is a non-aromatic $C_{1-4}$ hydrocarbon group which is optionally substituted with one or more groups selected from fluorine; chlorine; bromine; cyano; hydroxy; methoxy; amino; or a cycloalkyl, heterocycloalkyl, aryl or heteroaryl group;
and the dotted line indicates an optional second carbon-carbon bond, provided that when a second carbon-carbon bond is present, then $R^3$ is absent.

Particular compounds of the formula (1) are as defined in the Embodiments 1.2 to 1.104 set out below.

1.2 A compound according to Embodiment 1.1 wherein Q is an azetidine ring.

1.3 A compound according to Embodiment 1.1 wherein Q is a cyclobutyl ring.

1.4 A compound according to Embodiment 1.2 wherein Q is an azetidine ring linked to the adjacent five-membered, six-membered or seven membered ring by a carbon atom of the azetidine ring.

1.5 A compound according to Embodiment 1.2 wherein Q is an azetidine ring linked to the adjacent five-membered, six-membered or seven membered ring by the nitrogen atom of the azetidine ring.

1.6 A compound according to Embodiments 1.1 to 1.5 wherein Q is bicyclic; having a further ring attached to Q.

1.7 A compound according to any one of Embodiments 1.1 to 1.6 wherein $R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$ consisting of hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.8 A compound according to Embodiment 1.7 wherein $R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1 or 2 heteroatoms selected from O, N and S and oxidized forms thereof;

wherein the optional substituents for the optionally substituted 5- or 6-membered ring are selected from a group $R^8$ consisting of fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.9 A compound according to Embodiment 1.8 wherein $R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered aryl or heteroaryl ring containing 0, 1 or 2 heteroatoms selected from O, N and S and oxidized forms thereof;

wherein the optional substituents for the optionally substituted 5- or 6-membered aryl or heteroaryl ring are selected from a group R consisting of fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.10 A compound according to any one of Embodiments 1.1 to 1.9 wherein $R^1$ is selected from hydrogen; fluorine; chlorine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SO_2R^5$; a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof, wherein the optional substituents for the optionally substituted 5- or 6-membered ring are selected from a group $R^8$ consisting of fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.11 A compound according to Embodiment 1.10 wherein $R^1$ is selected from hydrogen; fluorine; chlorine; cyano; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.12 A compound according to Embodiment 1.11 wherein $R^1$ is selected from hydrogen; fluorine; chlorine; cyano; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $SO_2R^5$; and a $C_{1-4}$ non-aromatic hydrocarbon group which is optionally substituted with one to six fluorine atoms.

1.13 A compound according to Embodiment 1.12 wherein $R^1$ is selected from hydrogen; fluorine; chlorine; cyano; $NR^5R^6$; $COR^5$; $COOR^5$ and a $C_{1-6}$ non-aromatic hydrocarbon group which is optionally substituted with one to six fluorine atoms.

1.14 A compound according to Embodiment 1.13 wherein $R^1$ is selected from hydrogen; fluorine; chlorine; cyano;

NH$_2$, COR$^5$; COOR$^5$ and a C$_{1-4}$ saturated non-aromatic hydrocarbon group which is optionally substituted with one to six fluorine atoms.

1.15 A compound according to Embodiment 1.14 wherein R$^1$ is selected from hydrogen; COR$^5$; COOR$^5$; CONR$^5$R$^6$ and a C$_{1-4}$ alkyl group.

1.16 A compound according to Embodiment 1.15 wherein R$^1$ is selected from hydrogen; COR$^5$; COOR$^5$ and a C$_{1-3}$ alkyl group.

1.17 A compound according to Embodiment 1.16 wherein R$^1$ is selected from hydrogen; methyl; ethyl and COOR$^5$.

1.18 A compound according to Embodiment 1.17 wherein R$^1$ is hydrogen.

1.19 A compound according to Embodiment 1.17 wherein R$^1$ is methyl or ethyl.

1.20 A compound according to Embodiment 1.7 to 1.17 wherein R$^1$ is COOMe; COOEt; COMe; COEt; CONH$_2$; CF$_3$; CONHMe; CON(Me)$_2$; COCF$_3$; CO-cyclopropyl; CO-cyclobutyl; CONHEt; COH; NH$_2$; OMe;

1.21 A compound according to any one of the Embodiments 1.1 to 1.20 wherein R$^{2'}$ is selected from hydrogen; fluorine; chlorine; bromine; cyano; hydroxy; methoxy; and a C$_{1-6}$ non-aromatic hydrocarbon group; or is joined together with R$^1$ to form a 6 membered fused aromatic ring.

1.22 A compound according to Embodiment 1.21 wherein R$^{2'}$ is selected from hydrogen; fluorine; hydroxy; methoxy; and a C$_{1-6}$ non-aromatic hydrocarbon group.

1.23 A compound according to Embodiment 1.22 wherein R$^{2'}$ is selected from hydrogen; fluorine; methoxy; and a C$_{1-4}$ saturated hydrocarbon group.

1.24 A compound according to Embodiment 1.23 wherein R$^{2'}$ is selected from hydrogen; fluorine; methoxy; and a C$_{1-4}$ alkyl group.

1.25 A compound according to Embodiment 1.24 wherein R$^{2'}$ is selected from hydrogen and a C$_{1-3}$ alkyl group.

1.26 A compound according to Embodiment 1.25 wherein R$^{2'}$ is selected from hydrogen and methyl.

1.27 A compound according to Embodiment 1.21 wherein R$^{2'}$ is joined together with R$^1$ to form a 4 to 7 membered fused ring.

1.28 A compound according to Embodiment 1.27 wherein R$^{2'}$ is joined together with R$^1$ to form a 5 or 6 membered fused aromatic ring which may be aryl or heteroaryl.

1.29 A compound according to any one of the Embodiments 1.1 to 1.28 wherein R$^{2''}$ is selected from hydrogen; fluorine; chlorine; bromine; cyano; hydroxy; methoxy; and a C$_{1-6}$ non-aromatic hydrocarbon group; or is joined together with R$^1$ to form a 6 membered fused aromatic ring.

1.30 A compound according to Embodiment 1.29 wherein R$^{2''}$ is selected from hydrogen; fluorine; hydroxy; methoxy; and a C$_{1-6}$ non-aromatic hydrocarbon group.

1.31 A compound according to Embodiment 1.30 wherein R$^{2''}$ is selected from hydrogen; fluorine; methoxy; and a C$_{1-4}$ saturated hydrocarbon group.

1.32 A compound according to Embodiment 1.31 wherein R$^{2''}$ is selected from hydrogen; fluorine; methoxy; and a C$_{1-4}$ alkyl group.

1.33 A compound according to Embodiment 1.32 wherein R$^{2''}$ is selected from hydrogen and a C$_{1-3}$ alkyl group.

1.34 A compound according to Embodiment 1.33 wherein R$^{2''}$ is selected from hydrogen and methyl.

1.35 A compound according to any one of Embodiments 1.1 to 1.34 wherein the dotted line represents a second carbon-carbon bond and R$^3$ is absent.

1.36 A compound according to any one of Embodiments 1.1 to 1.34 wherein R$^3$ is present and the optional second carbon-carbon bond is absent.

1.37 A compound according to Embodiment 1.36 wherein R$^3$ is selected from hydrogen; fluorine; cyano; hydroxy; amino; and a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.38 A compound according to Embodiment 1.37 wherein R$^3$ is selected from hydrogen; fluorine; cyano; hydroxy; amino; and a C$_{1-6}$ non-aromatic hydrocarbon group which is optionally substituted with one to six fluorine atoms and wherein one, but not all, carbon atoms of the hydrocarbon group may optionally be replaced by a heteroatom selected from O, N and S and oxidized forms thereof.

1.39 A compound according to Embodiment 1.38 wherein R$^3$ is selected from hydrogen; fluorine; cyano; hydroxy; amino; C$_{1-4}$ alkyl and C$_{1-4}$ alkoxy, wherein the C$_{1-4}$ alkyl and C$_{1-4}$ alkoxy are each optionally substituted with one to six fluorine atoms.

1.40 A compound according to Embodiment 1.39 wherein R$^3$ is selected from hydrogen; fluorine; hydroxy and methoxy.

1.41 A compound according to Embodiment 1.40 wherein R$^3$ is hydrogen.

1.42 A compound according to any one of Embodiments 1.1 to 1.41 wherein R$^4$ is hydrogen or an acyclic C$_{1-6}$ hydrocarbon group.

1.43 A compound according to Embodiment 1.42 wherein R$^4$ is hydrogen or an acyclic C$_{1-3}$ hydrocarbon group.

1.44 A compound according to Embodiment 1.43 wherein R$^4$ is hydrogen or a C$_{1-3}$ alkyl group or a C$_{2-3}$ alkynyl group.

1.45 A compound according to Embodiment 1.44 wherein R$^4$ is selected from hydrogen, methyl, ethyl, ethynyl and 1-propynyl.

1.46 A compound according to Embodiment 1.45 wherein R$^4$ is selected from hydrogen and methyl.

1.47 A compound according to Embodiment 1.46 wherein R$^4$ is methyl.

1.48 A compound according to any one of the preceding Embodiments wherein R$^5$, when present, is a non-aromatic C$_{1-4}$ hydrocarbon group optionally substituted with one or more fluorine atoms; or a group of formula CH$_2$N(R$^a$)OOR$^b$.

1.49 A compound according to Embodiment 1.48 wherein the non-aromatic C$_{1-4}$ hydrocarbon group is a saturated C$_{1-4}$ hydrocarbon group.

1.50 A compound according to any one of Embodiments 1.1 to 1.49 wherein R$^5$, when present, is hydrogen.

1.51 A compound according to any one of Embodiments 1.1 to 1.48 wherein R$^5$, when present, is selected from hydrogen and a saturated C$_{1-4}$ hydrocarbon group.

1.52 A compound according to Embodiment 1.51 wherein the saturated C$_{1-4}$ hydrocarbon group is a C$_{1-4}$ alkyl group.

1.53 A compound according to Embodiment 1.52 wherein the saturated C$_{1-4}$ hydrocarbon group is a C$_{1-3}$ alkyl group.

1.54 A compound according to Embodiment 1.53 wherein the C$_{1-3}$ alkyl group is selected from methyl, ethyl and isopropyl.

1.55 A compound according to Embodiment 1.54 wherein the C$_{1-3}$ alkyl group is ethyl.

1.56 A compound according to any one of the preceding Embodiments wherein R$^6$, when present, is a non-aromatic C$_{1-4}$ hydrocarbon group.

1.57 A compound according to Embodiment 1.56 wherein the non-aromatic C$_{1-4}$ hydrocarbon group is a saturated C$_{1-4}$ hydrocarbon group.

1.58 A compound according to any one of Embodiments 1.1 to 1.54 wherein R⁶, when present, is hydrogen.

1.59 A compound according to Embodiment 1.57 wherein the saturated C$_{1-4}$ hydrocarbon group is a C$_{1-3}$ alkyl group.

1.60 A compound according to Embodiment 1.59 wherein the C$_{1-3}$ alkyl group is selected from methyl, ethyl and isopropyl.

1.61 A compound according to any one of the preceding Embodiments wherein R⁷, when present, is a non-aromatic C$_{1-4}$ hydrocarbon group.

1.62 A compound according to Embodiment 1.61 wherein the non-aromatic C$_{1-4}$ hydrocarbon group is a saturated C$_{1-4}$ hydrocarbon group.

1.63 A compound according to any one of Embodiments 1.1 to 1.60 wherein R⁷, when present, is hydrogen.

1.64 A compound according to any one of Embodiments 1.1 to 1.60 wherein R⁷, when present, is selected from hydrogen and a saturated C$_{1-4}$ hydrocarbon group.

1.65 A compound according to Embodiment 1.62 or Embodiment 1.64 wherein the saturated C$_{1-4}$ hydrocarbon group is a C$_{1-4}$ alkyl group.

1.66 A compound according to Embodiment 1.65 wherein the saturated C$_{1-4}$ hydrocarbon group is a C$_{1-3}$ alkyl group.

1.67 A compound according to Embodiment 1.66 wherein the C$_{1-3}$ alkyl group is selected from methyl, ethyl and isopropyl.

1.68 A compound according to any one of the preceding Embodiments wherein, when R¹ is an optionally substituted 5- or 6-membered ring, it is selected from aromatic rings containing 0, 1 or 2 or 3 heteroatoms selected from O, N and S and oxidized forms thereof.

1.69 A compound according to Embodiment 1.68 wherein the aromatic ring is carbocyclic.

1.70 A compound according to Embodiment 1.69 wherein the aromatic ring is heterocyclic.

1.71 A compound according to any one of Embodiments 1.1 to 1.67 wherein, when R¹ is an optionally substituted 5- or 6-membered ring, it is selected from non-aromatic rings containing 0, 1 or 2 or 3 heteroatoms selected from O, N and S and oxidized forms thereof.

1.72 A compound according to Embodiment 1.71 wherein the non-aromatic ring is carbocyclic.

1.73 A compound according to Embodiment 1.72 wherein the non-aromatic ring is heterocyclic.

1.74 A compound according to any one of Embodiments 1.68 to 1.73 wherein the ring is a 5-membered ring.

1.75 A compound according to any one of Embodiments 1.68 to 1.73 wherein the ring is a 6-membered ring.

1.76 A compound according to any one of the preceding Embodiments wherein, when R¹ is an optionally substituted 5- or 6-membered ring, it is substituted with 0, 1, 2 or 3 substituents R⁸.

1.77 A compound according to Embodiment 1.76 wherein there are 0, 1 or 2 substituents R⁸ present.

1.78 A compound according to Embodiment 1.77 wherein there are 0 substituents R⁸ present.

1.79 A compound according to Embodiment 1.77 wherein there is 1 substituent R⁸ present.

1.80 A compound according to Embodiment 1.77 wherein there are 2 substituents R⁸ present.

1.81 A compound according to any one of Embodiments 1.76, 1.77, 1.79, and 1.80 wherein R⁸ when present is selected from fluorine; cyano; oxo; hydroxy; OR⁵; NR⁵R⁶; COR⁵; COOR⁵; OCOR⁵; NR⁷COR⁵; CONR⁵R⁶; SR⁵; SOR⁵ and SO$_2$R⁵; and a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.82 A compound according to Embodiment 1.81 wherein R⁸ is selected from fluorine; cyano; oxo; hydroxy; OR⁵; NR⁵R⁶; COR⁵; COOR⁵; OCOR⁵ and SO$_2$R⁵; and a C$_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.83 A compound according to Embodiment 1.82 wherein R⁸ is selected from fluorine; cyano; oxo; hydroxy; OR⁵; NR⁵R⁶; and a C$_{1-4}$ non-aromatic hydrocarbon group which is optionally substituted with one to six fluorine atoms.

1.84 A compound according to Embodiment 1.83 wherein R⁸ is selected from cyano; oxo; hydroxy; OR⁵; NR⁵R⁶; and C$_{1-4}$ alkyl.

1.85 A compound according to any one of Embodiments 1.1 to 1.84 wherein q is 0.

1.86 A compound according to any one of Embodiments 1.1 to 1.84 wherein q is 1.

1.87 A compound according to any one of Embodiments 1.1 to 1.84 wherein q is 2.

1.88 A compound according to any one of Embodiments 1.1 to 1.87 wherein r is 1.

1.89 A compound according to any one of Embodiments 1.1 to 1.88 wherein s is 0.

1.90 A compound according to any one of Embodiments 1.1 to 1.88 wherein r is 1 and s is 1.

1.91 A compound according to any one of Embodiments 1.1 to 1.87 wherein r is 2 and s is 0.

1.92 A compound according to any one of Embodiments 1.1 to 1.891 wherein the moiety:

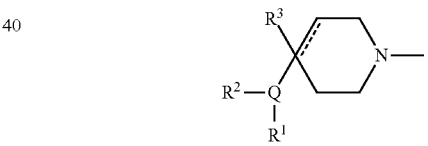

is selected from groups A to F below:

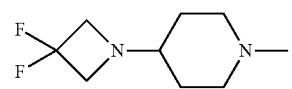

A

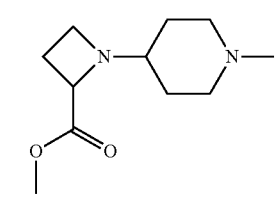

B

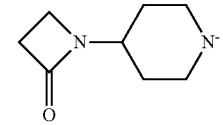

C

-continued

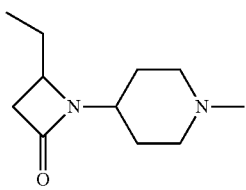

D

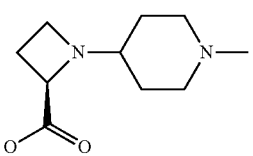

E

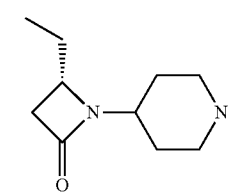

F 1.92 A compound according to having the formula (2):

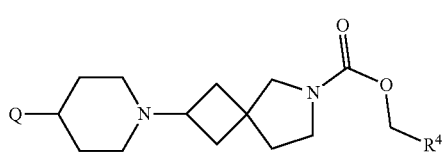

(2)

wherein Q is an optionally substituted 4 membered ring, and $R^4$ is as defined in any one of Embodiments 1.35 to 1.40.

1.93 A compound according to formula (2) wherein Q has one or more substituents, for example one, or two substituents which are selected from (L)-$R^{10}$, (L)-$R^{11}$ and (L)-$R^{12}$, where L is a bond or a $CH_2$ group; $R^{10}$, $R^{11}$ and $R^{12}$ are independently selected from hydrogen; fluorine; chlorine; bromine; cyano; oxo; hydroxy; OR; $NR^{15}R^{16}$; $COR^{15}$; $CSR^{15}$; $COOR^{15}$; $COSR^{15}$; $OCOR^{15}$; $NR^1COR^{15}$; $CONR^{15}R^{16}$; $CSNR^{15}R^{16}$; $NR^{17}CONR^{15}R^{16}$; $R^{17}COOR^{15}$; $OCONR^{15}R^{16}$; $SR^{15}$; $SOR^{15}$ and $SO_2R^{15}$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$ consisting of hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

wherein $R^{15}$, $R^{16}$ and $R^{17}$ are the same or different, or may be joined together to form a ring, and each is independently selected from hydrogen, a non-aromatic $C_{1-6}$ hydrocarbon group optionally substituted with one or more fluorine atoms and wherein one or two, but not all, carbon atoms of the hydrocarbon group may optionally be replaced by a heteroatom selected from O, N and S and oxidized forms thereof; or a group of formula $CH_2N(R^a)COOR^b$; or a group of formula (L)-$R^{18}$ where L is a bond or a $CH_2$ group and $R^{18}$ is an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$.

1.94 A compound according to Embodiments 1.1 to 1.93 having the formula (3):

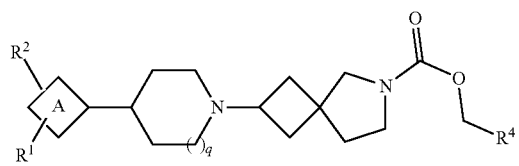

(3)

wherein q, $R^1$, $R^2$ and $R^4$ are as defined in any one preceding embodiment and the ring A is cyclobutyl or azetidine.

1.95 A compound according to Embodiment 1.94 wherein the ring A is cyclobutyl.

1.96 A compound according to Embodiment 1.95 wherein the ring A is azetidine.

1.97 A compound according to Embodiment 1.96 having the formula (4):

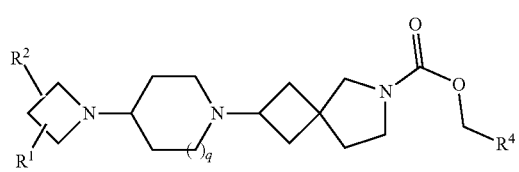

(4)

wherein q, $R^1$, $R^2$ and $R^4$ are as defined in any one preceding Embodiment.

1.98 A compound according to Embodiment 1.1 which is as defined in any one of Examples 1-1 to 1-7.

1.99 A compound according to any one of Embodiments 1.1 to 1.97 having a molecular weight of less than 550.

1.100 A compound according to Embodiment 1.99 having a molecular weight of less than 500.

1.101 A compound according to Embodiment 1.100 having a molecular weight of, or less than 450.

1.102 A compound according to any one of Embodiments 1.1 to 1.101 which is in the form of a salt.

1.103 A compound according to Embodiment 1.102 wherein the salt is an acid addition salt.

1.104 A compound according to Embodiment 1.102 or Embodiment 1.103 wherein the salt is a pharmaceutically acceptable salt.

DEFINITIONS

In this application, the following definitions apply, unless indicated otherwise.

The term "treatment", in relation to the uses of the compounds of the formula (1), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" as in "$C_{1-10}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" aryl, heteroaryl and "cycloalkenyl" are used in their conventional sense (e.g. as defined in the IUPAC Gold Book) unless indicated otherwise.

The term "saturated hydrocarbon group" as in "$C_{1-4}$ saturated hydrocarbon group" refers to a hydrocarbon group containing no carbon-carbon double bonds or triple bonds. The saturated hydrocarbon group can therefore be an alkyl group, a cycloalkyl group, a cycloalkylalkyl group, an alkylcycloalkyl group or a alkylcycloalkylalkyl group. Examples of $C_{1-4}$ saturated hydrocarbon groups include $C_{1-4}$ alkyl groups, cyclopropyl, cyclobutyl and cyclopropylmethyl.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^2$, $R^3$ and $R^4$ above, where stated, one or two but not all, carbon atoms of the non-aromatic hydrocarbon group may optionally be replaced by a heteroatom selected from O, N and S and (in the case of $R^1$ and $R^4$) oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—$S(O)_2$—$CH_2$—, replacement of a carbon atom in a —$CH_2$—$CH_2$—$CH_2$— chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) can exist in the form of salts, for example acid addition salts or, in certain cases salts of organic and inorganic bases such as carboxylate, sulfonate and phosphate salts. All such salts are within the scope of this invention, and references to compounds of the formula (1) include the salt forms of the compounds as defined in Embodiments 1.102 to 1.104.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.120) may be formed with a wide variety of acids, both inorganic and organic. Examples of acid addition salts falling within Embodiment 1.120 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) contain an amine function, these may form quaternary ammonium salts, for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.121), the invention provides a geometric isomer of a compound according to any one of Embodiments 1.1 to 1.104.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.132) the invention provides a compound according to any one of Embodiments 1.1 to 1.121 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.133), the invention provides compositions containing a compound according to Embodiment 1.132 having one or more chiral centres, wherein at least 55% (e.g. at least 60%, 65%, 70%, 75%, 80%, 85%, 90% or 95%) of the compound of Embodiment 1.108 is present as a single optical isomer (e.g. enantiomer or diastereoisomer).

In one general embodiment (Embodiment 1.134), 99% or more (e.g. substantially all) of the total amount of the compound (or compound for use) of Embodiment 1.132 is present as a single optical isomer.

For example, in one embodiment (Embodiment 1.135) the compound is present as a single enantiomer.

In another embodiment (Embodiment 1.136), the compound is present as a single diastereoisomer.

The invention also provides mixtures of optical isomers, which may be racemic or non-racemic. Thus, the invention provides:

1.137 A compound according to Embodiment 1.132 which is in the form of a racemic mixture of optical isomers.

1.138 A compound according to Embodiment 1.132 which is in the form of a non-racemic mixture of optical isomers.

Isotopes

The compounds of the invention as defined in any one of Embodiments 1.1 to 1.138 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.140), the compound of any one of Embodiments 1.1 to 1.138 contains no radioactive isotopes. Such compounds are preferred for therapeutic use. In another embodiment (Embodiment 1.141), however, the compound of any one of Embodiments 1.1 to 1.138 may contain one or more radioisotopes. Compounds containing such radioisotopes may be useful in a diagnostic context.

Solvates

Compounds of the formula (1) as defined in any one of Embodiments 1.1 to 1.141 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.150 and 1.151, the invention provides:

1.151 A compound according to any one of Embodiments 1.1 to 1.141 in the form of a solvate.

1.152 A compound according to Embodiment 1.151 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.153), the invention provides a compound as defined in any one of Embodiments 1.1 to 1.141 in an anhydrous form (e.g. anhydrous crystalline form).

Crystalline and Amorphous Forms

The compounds of any one of Embodiments 1.1 to 1.153 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.160 A compound according to any one of Embodiments 1.1 to 1.153 in a crystalline form.

1.161 A compound according to any one of Embodiments 1.1 to 1.153 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.162 A compound according to any one of Embodiments 1.1 to 1.153 which is in an amorphous form.

Prodrugs

The compounds of the formula (1) as defined in any one of Embodiments 1.1 to 1.162 may be presented in the form of a pro-drug. By "prodrugs" is meant for example any compound that is converted in vivo into a biologically active compound of the formula (1), as defined in any one of Embodiments 1.1 to 1.162.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.170), the invention provides a pro-drug of a compound as defined in any one of Embodiments 1.1 to 1.170 wherein the compound contains a functional group which is convertable under physiological conditions to form a hydroxyl group or amino group.

Complexes and Clathrates

Also encompassed by formula (1) in Embodiments 1.1 to 1.170 are complexes (e.g. inclusion complexes or clathrates with compounds such as cyclodextrins, or complexes with metals) of the compounds of Embodiments 1.1 to 1.170.

Accordingly, in another embodiment (Embodiment 1.180), the invention provides a compound according to any one of Embodiments 1.1 to 1.170 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptor relative to the $M_2$ and $M_3$ receptor subtypes.

Compounds of the invention are not agonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ and/or $M_4$ receptor in the functional assay described in Example A, they may have $pEC_{50}$ values of less than 5 and $E_{max}$ values of less than 20% when tested against the $M_2$ and $M_3$ subtypes in the functional assay of Example A.

Accordingly, in Embodiments 2.1 to 2.9, the invention provides:

2.1 A compound according to any one of Embodiments 1.1 to 1.180 for use in medicine.

2.2 A compound according to any one of Embodiments 1.1 to 1.180 for use as a muscarinic $M_1$ and/or $M_4$ receptor agonist.

2.3 A compound according to any one of Embodiments 1.1 to 1.180 which is a muscarinic $M_1$ receptor agonist having a $pEC_5$ in the range from 6.0 to 7.5 and an $E_{max}$ of at least 90 against the $M_1$ receptor in the assay of Example A herein or an assay substantially similar thereto.

2.4 A compound according to Embodiment 2.3 which is a muscarinic $M_1$ receptor agonist having a $pEC_{50}$ in the range from 6.5 to 7.5.

2.5 A compound according to Embodiment 2.3 or Embodiment 2.4 having an $E_{max}$ of at least 95 against the $M_1$ receptor.

2.6 A compound according to any one of Embodiments 1.1 to 1.180 which is a muscarinic $M_4$ receptor agonist having a $pEC_5$ in the range from 6.0 to 8.0 and an $E_{max}$ of at least 90 against the $M_4$ receptor in the assay of Example A herein or an assay substantially similar thereto.

2.7 A compound according to Embodiment 2.6 which is a muscarinic $M_4$ receptor agonist having a $pEC_{50}$ in the range from 6.5 to 8.0.

2.8 A compound according to Embodiment 2.6 or Embodiment 2.7 having an $E_{max}$ of at least 95 against the $M_4$ receptor.

2.9 A compound according to any one of Embodiments 2.3 to 2.8 which is selective for the $M_1$ and/or $M_4$ receptor compared to the muscarinic $M_2$ and $M_3$ receptors.

2.10 A compound according to Embodiment 2.9 which is selective for the $M_1$ receptor compared to the muscarinic $M_2$ and $M_3$ receptors.

2.11 A compound according to Embodiment 2.9 which is selective for the $M_4$ receptor compared to the muscarinic $M_2$ and $M_3$ receptors.

2.12 A compound according to any one of Embodiments 2.3 to 2.5 which is selective for the $M_1$ receptor compared to the muscarinic $M_2$, $M_3$ and $M_4$ receptors.

2.13 A compound according to any one of Embodiments 2.6 to 2.8 which is selective for the $M_4$ receptor compared to the muscarinic $M_1$, $M_2$ and $M_3$ receptors.

2.14 A compound according to any one of Embodiments 2.3 to 2.8 which is selective for the $M_1$ and $M_4$ receptor compared to the muscarinic $M_2$ and $M_3$ receptors.

2.15 A compound according to any one of Embodiments 2.3 to 2.14 which has a $pEC_{50}$ of less than 5 and an $E_{max}$ of less than 50 against the muscarinic $M_2$ and $M_3$ receptor subtypes.

2.16 A compound according to Embodiment 2.15 which has a $pEC_{50}$ of less than 4.5 and/or an $E_{max}$ of less than 30 against the muscarinic $M_2$ and $M_3$ receptor subtypes.

2.17 A compound according to any one of Embodiments 1.1 to 1.180 and Embodiments 2.3 to 2.16 for use in the treatment of a disease or condition mediated by the muscarinic $M_1$ receptor.

By virtue of their muscarinic $M_1$ and/or $M_4$ receptor agonist activity, compounds of the invention can be used in the treatment of Alzheimer's disease, schizophrenia and other psychotic disorders, cognitive disorders and other diseases mediated by the muscarinic $M_1$ and/or $M_4$ receptor, and can also be used in the treatment of various types of pain.

Accordingly, in Embodiments 2.18 to 2.37, the invention provides:

2.18 A compound according to any one of Embodiments 1.1 to 1.180 for use in the treatment of a cognitive disorder or psychotic disorder.

2.19 A compound for use in according to Embodiment 2.18 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders, epilepsy and schizo-affective disorder.

2.20 A compound according to any one of Embodiments 1.1 to 1.180 for use in the treatment of Alzheimer's disease.

2.21 A compound according to any one of Embodiments 1.1 to 1.180 for use in the treatment of Schizophrenia.

2.22 A compound according to any one of Embodiments 1.1 to 1.180 for use in the treatment of Alzheimer's disease and/or dementia with Lewy bodies.

2.23 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.180.

2.24 A method according to Embodiment 2.20 wherein the cognitive disorder comprises, arises from or is associated with a condition as defined in Embodiment 2.19.

2.25 A method according to Embodiment 2.24 wherein the cognitive disorder arises from or is associated with Alzheimer's disease.

2.26 A method according to Embodiment 2.24 wherein the cognitive disorder is Schizophrenia.

2.27 The use of a compound according to any one of Embodiments 1.1 to 1.180 for the manufacture of a medicament for the treatment of a cognitive disorder.

2.28 The use according to Embodiment 2.27 wherein the cognitive disorder comprises, arises from or is associated with a condition as defined in Embodiment 2.11.

2.29 The use according to Embodiment 2.28 wherein the cognitive disorder arises from or is associated with Alzheimer's disease.

2.30 The use according to Embodiment 2.28 wherein the cognitive disorder is Schizophrenia.

2.31 A compound according to any one of Embodiments 1.1 to 1.180 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.32 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.180.

2.33 A compound according to any one of Embodiments 1.1 to 1.180 for the treatment of peripheral disorders such as reduction of intra ocular pressure in Glaucoma and treatment of dry eyes and dry mouth including Sjogren's Syndrome.

2.34 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.180.

2.35 The use of a compound according to any one of Embodiments 1.1 to 1.180 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.36 The use of a compound according to any one of Embodiments 1.1 to 1.180 for the treatment of addiction.

2.37 The use of a compound according to any one of Embodiments 1.1 to 1.180 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.180, which process comprises:

(A) the reaction of a compound of the formula (10)

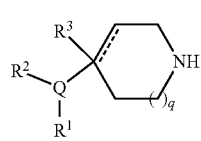

(10)

with a compound of the formula (11):

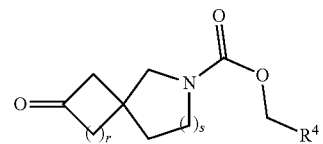

(11)

under reductive amination conditions; wherein $R^1$, $R^2$, $R^3$, $R^4$ and Q are as defined in any one of Embodiments 1.1 to 1.180; or (B) the reaction of a compound of the formula (12):

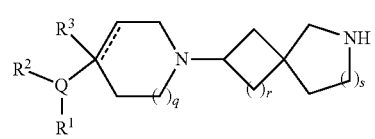

(12)

with a compound of the formula Cl—C(=O)—CH$_2$—R$^4$, in the presence of a base; or (C) the reaction of a compound of the formula (10)

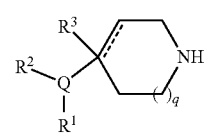

(10)

with a compound of the formula (13):

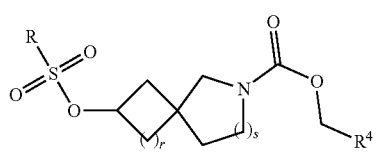

(13)

under nucleophilic substitution conditions; wherein $R^1$, $R^2$, $R^3$, $R^4$ and Q are as defined in any one of Embodiments 1.1 to 1.180; and optionally:

(D) converting one compound of the formula (1) to another compound of the formula (1).

In process variant (A), the piperidine heterocycle (10) is reacted with the substituted ketone (11) under reductive amination conditions. The reductive amination reaction is typically carried out at ambient temperature using a borohydride reducing agent such as sodium triacetoxy-borohydride in a solvent such as dichloromethane or dichloroethane containing acetic acid.

In process variant (C), the piperidine heterocycle (10) is reacted with the sulfonic ester (13, R=methyl, trifluoromethyl or 4-methylphenyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide.

Intermediate compounds of the formula (12) can be prepared by the series of reactions shown in Scheme 1 below.

Scheme 1

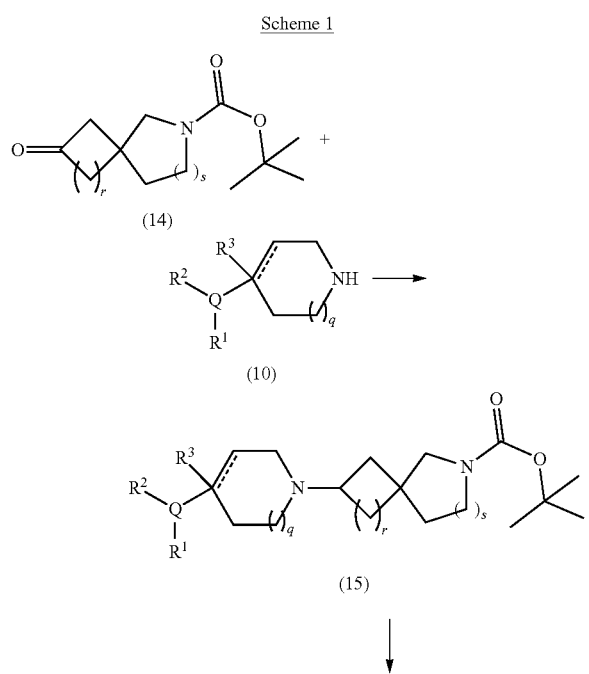

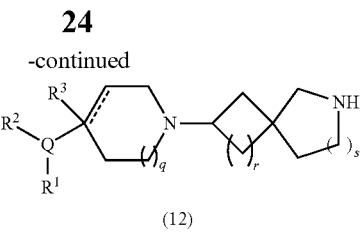

In reaction Scheme 1, the piperidine heterocycle (10) is reacted with the Boc-protected spiroketone (14) under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate piperidine compound (15) which is then deprotected by removal of the Boc group by treatment with acid (e.g. trifluoroacetic acid in dichloromethane) to give the compound (12).

Compounds of the formula (12) can also be prepared by the sequence of reactions shown in Scheme 2 below.

Scheme 2

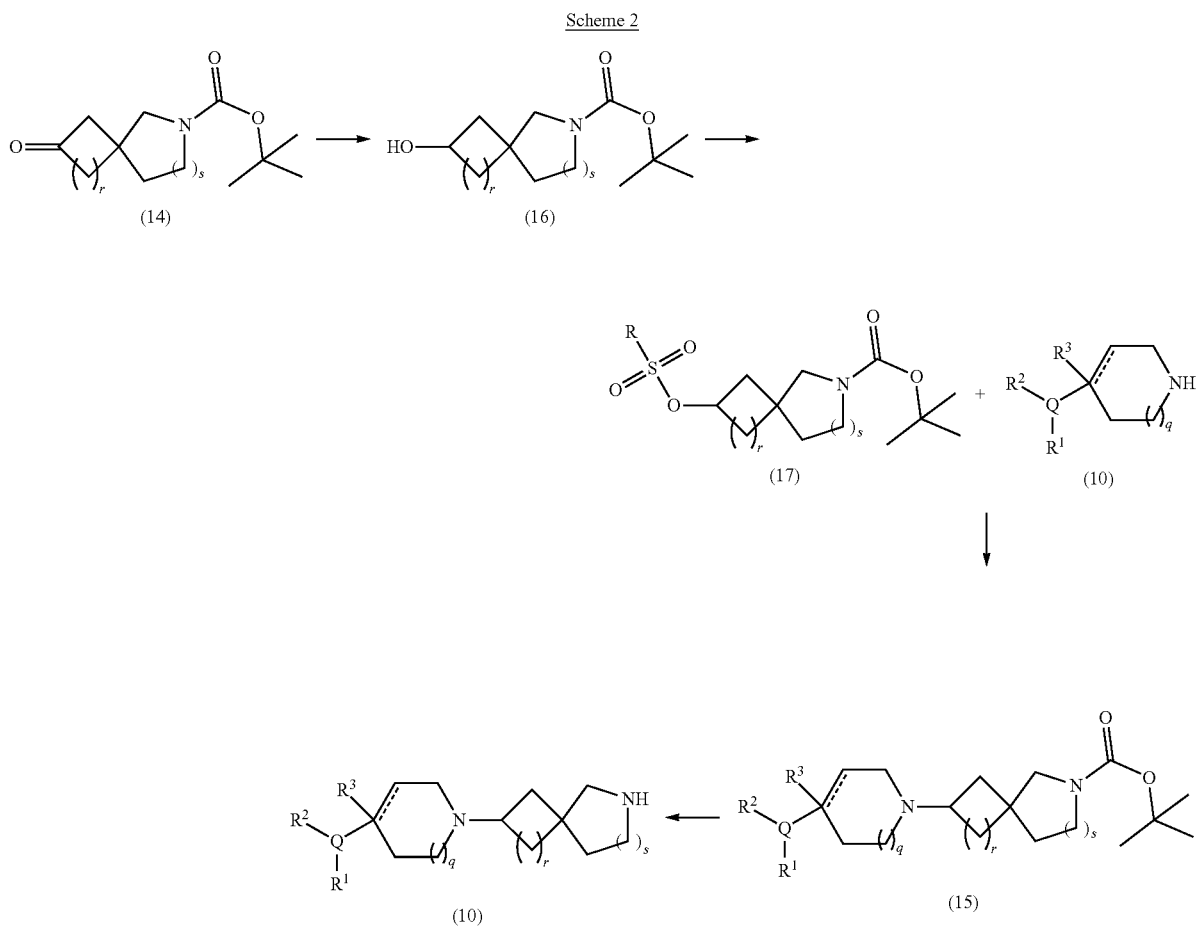

In Scheme 2, the Boc-protected spiroketone (14) is reduced to the alcohol (16) using sodium borohydride in methanol. The alcohol (16) is then activated as the sulfonic ester (17, R=methyl, trifluoromethyl or 4-methylphenyl) using the corresponding sulfonyl chloride in dichloromethane in the presence of a tertiary amine such as triethylamine or N,N-diisopropylethylamine. The sulfonic ester (17) is reacted with the piperidine heterocycle (10) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide to give compound (15) which is then deprotected by removal of the Boc group by treatment with acid (e.g. trifluoroacetic acid in dichloromethane) to give the compound (12).

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2). Examples of these transformations include amide bond formation, urea formation, carbamate formation, alkylation reactions, N-arylation reaction and C—C bond coupling reactions.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.180 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose).

They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 1-9

The compounds of Examples 1-1 to 1-9 shown in Table 1 below have been prepared. Their NMR and LCMS properties and the methods used to prepare them are set out in Table 3.

TABLE 1

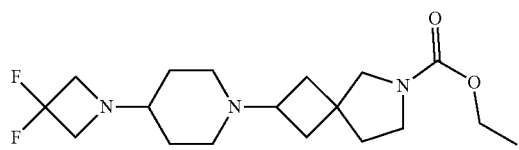 [SMILES: CCOC(=O)N1CCC2(CC(N3CCC(N4CC(F)(F)C4)CC3)C2)C1]

Example 1-1

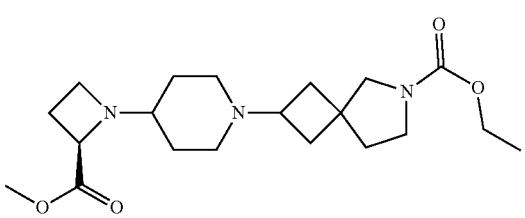 [SMILES: CCOC(=O)N1CCC2(CC(N3CCC(N4CC[C@@H]4C(=O)OC)CC3)C2)C1]

TABLE 1-continued

Example 1-2

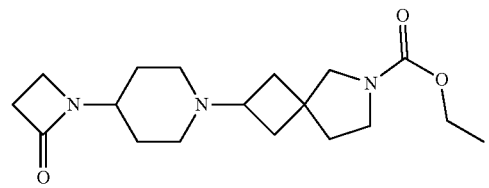 [SMILES: CCOC(=O)N1CCC2(CC(N3CCC(N4CCC4=O)CC3)C2)C1]

Example 1-3

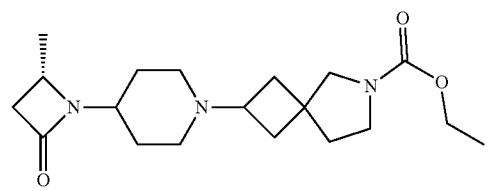 [SMILES: CCOC(=O)N1CCC2(CC(N3CCC(N4C(=O)C[C@@H]4C)CC3)C2)C1]

Example 1-4

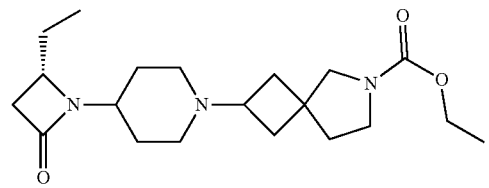 [SMILES: CCOC(=O)N1CCC2(CC(N3CCC(N4C(=O)C[C@@H]4CC)CC3)C2)C1]

Example 1-5

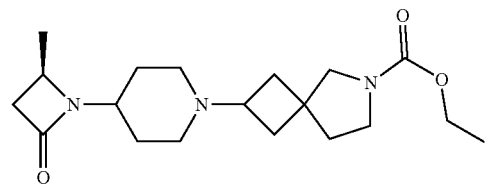 [SMILES: CCOC(=O)N1CCC2(CC(N3CCC(N4C(=O)C[C@H]4C)CC3)C2)C1]

Example 1-6

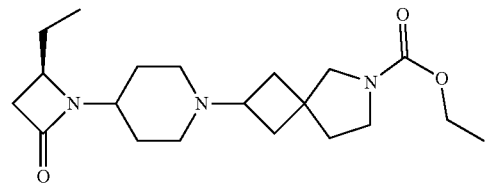 [SMILES: CCOC(=O)N1CCC2(CC(N3CCC(N4C(=O)C[C@H]4CC)CC3)C2)C1]

Example 1-7

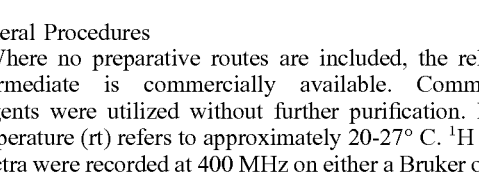

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ:)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and Silica gel F254 (Merck) as a stationary phase. Microwave-mediated reactions were performed in Biotage Initiator or CEM Discover microwave reactors.

LCMS experiments were typically carried out using electrospray conditions as specified for each compound under the following conditions:
LCMS Method A:
Instruments: Waters 2695, Photo Diode Array, ZQ-2000 Detector; Column: X-Bridge C18, 3.5 micron, 150×4.6 mm; Gradient [time (min)/solvent B in A (%)]: 0.00/5, 5.00/90, 5.80/95, 10/95; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.
LCMS Method B:
Instruments: Waters 2695, Photo Diode Array, ZQ-2000 Detector; Column: X-Bridge C18, 3.5 micron, 50×4.6 mm; Gradient [time (min)/solvent B in A (%)]: 0.01/0, 0.20/0, 5.00/90, 5.80/95, 7.20/95, 7.21/100, 10.00/100; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.
LCMS Method C
Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/5, 2.00/95, 2.50/95, 2.60/5, 3.00/5; Solvents: solvent A=2.5 L $H_2O$+2.5 mL of (28% $NH_3$ in $H_2O$); solvent B=2.5 L MeCN+129 mL $H_2O$+2.7 mL of (28% $NH_3$ in $H_2O$); Injection volume 0.5 µL; UV detection 190 to 400 nM; column temperature 40° C.; Flow rate 1.5 mL/min.
LCMS Methods D and E
Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method D: 0.00/2, 0.10/2, 2.50/95, 3.50/95, 3.55/2, 4.00/2 or Method E: 0.00/2, 0.10/2, 8.40/95, 9.40/95, 9.50/2, 10.00/2; Solvents: solvent C=2.5 L $H_2O$+2.5 mL 28% ammonia in $H_2O$ solution; solvent D=2.5 L MeCN+135 mL $H_2O$+2.5 mL 28% ammonia in $H_2O$ solution); Injection volume 1 µL; UV detection 230 to 400 nM; Mass detection 130 to 800 AMU (+ve and −ve electrospray); column temperature 45° C.; Flow rate 1.5 mL/min.

LCMS data in the experimental section are given in the format: Mass ion, retention time, UV activity.
Abbreviations
AcOH=acetic acid
CDI=1,1'-Carbonyldiimidazole
d=day(s)
DAST=diethylaminosulfur trifluoride
DCE=dichloroethane
DCM=dichloromethane
DIPEA=diisopropylethylamine
DIAD=diisopropyl azodicarboxylate
DMF=dimethylformamide
DMP=Dess-Martin periodinane
DMSO=dimethylsulfoxide
ES=electro spray ionisation
EtOAc=ethyl acetate
h=hour(s)
HATU=1-[Bis(dimethylamino)methylene]-1H-1,2,3-triazolo[4,5-b]pyridinium 3-oxid hexafluorophosphate
HPLC=high performance liquid chromatography
LC=liquid chromatography
$LiAlH_4$/LAH=Lithium aluminium hydride
MeCN=acetonitrile
MeOH=methanol
min=minute(s)
MS=mass spectrometry
$Et_3N$=triethylamine
NMR=nuclear magnetic resonance
rt=room temperature
sat.=saturated
sol.=solution
STAB=sodium triacetoxyborohydride
THF=tetrahydrofuran
TLC=thin layer chromatography
Prefixes n-, s-, i-, t- and tert- have their usual meanings: normal, secondary, iso, and tertiary.
General Synthetic Procedures for Intermediates:
Route 1

Procedure for the Preparation of Intermediate 2, ethyl 2-oxo-6-azaspiro[3.4]octane-6-carboxylate

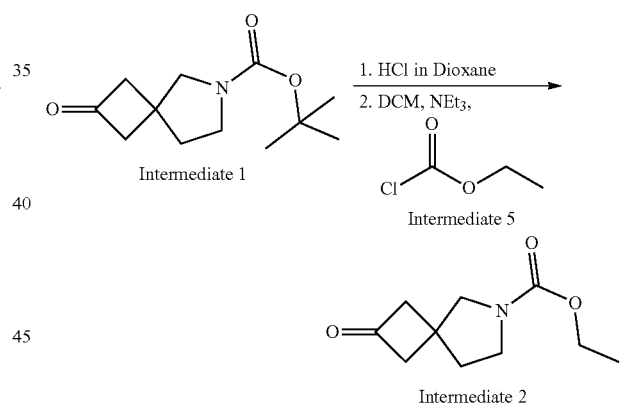

6-Boc-2-oxo-6-azaspiro[3.4]octane (3.37 g, 15 mmol) was added portionwise to hydrogen chloride (4 M dioxane solution, 50 mL, 210 mmol). Caution: effervescence. After 24 h, the reaction was concentrated in vacuo and the residual solid was dissolved in a mixture of $Et_3N$ (4.18 ml, 30 mmol) and DCM (66 mL). On completion of dissolution, the solution was immediately cooled to 0° C., then ethyl chloroformate (1.57 mL, 16.5 mmol) was added dropwise. After 18 h, the mixture was poured into dichloromethane (100 mL) and $NaHCO_3$ (aq) (100 mL) and extracted (2×100 mL). The organic layers were collected, washed with brine (20 mL), dried over $MgSO_4$, then the residue after evaporation was purified by column chromatography (normal phase, [Biotage SNAP cartridge KP-sil 100 g, 40-63 µm, 60 Å, 50 mL per min, gradient 0% to 4% MeOH in DCM]) to give Intermediate 2, ethyl 2-oxo-6-azaspiro[3.4]octane-6-carboxylate (2.47 g, 83%) as a colourless oil. The data for the title compound are in Table 2.

Route 2

Procedure for the Preparation of Intermediate 8, (4S)-4-ethyl-1-(piperidin-4-yl)azetidin-2-one

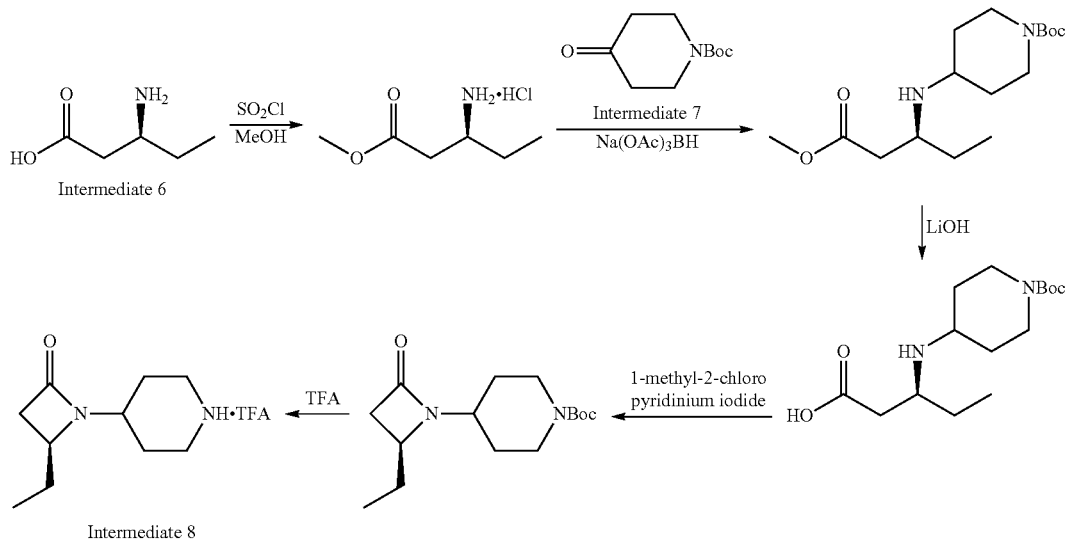

Intermediate 8

To a solution of MeOH (60 mL) at −10° C. was added thionyl chloride (1.25 mL, 17.1 mmol) dropwise, and the resulting mixture stirred at −10° C. for 1 h. (3S)-3-Aminopentanoic acid (1.0 g, 8.5 mmol) was then added in one portion and the resulting mixture stirred at rt for 20 h. The solvent was removed in vacuo to yield methyl (3S)-3-aminopentanoate.HCl (1.69 g) as a light brown oil, which was used crude in the next step.

LC/MS (method C): m/z 132 (M+H)+ (ES+), at 0.56 min, UV inactive.

To methyl (3S)-3-aminopentanoate.HCl (250 mg, assumed 1.3 mmol) in DMF (15 mL) was added DIPEA (1.30 mL, 7.5 mmol), AcOH (0.13 mL, 2.3 mmol), tert-butyl 4-oxopiperidine-1-carboxylate (297 mg, 1.5 mmol) and sodium triacetoxyborohydride (632 mg, 3.0 mmol) and the resulting mixture stirred at rt for 24 h. The solvent was then removed in vacuo and the residue purified on silica (Biotage Isolera, SNAP 25 g cartridge, 0-10% 0.7 M NH$_3$ in MeOH/DCM) and relevant fractions combined to yield tert-butyl 4-{[(3S)-1-methoxy-1-oxopentan-3-yl]amino}piperidine-1-carboxylate (1.14 g) as a yellow oil, which crystallized upon standing at rt to a white solid, and was used crude in the next step.

LC/MS (method C): m/z 315 (M+H)+ (ES+), at 1.40 min, UV active.

To a solution of crude tert-butyl 4-{[(3S)-1-methoxy-1-oxopentan-3-yl]amino}piperidine-1-carboxylate (1.14 g, assumed 1.3 mmol) in THF (30 mL) was added LiOH (313 mg, 7.5 mmol) and H$_2$O(7.5 mL) and the mixture stirred at rt for 65 h. The mixture was then heated to reflux for 2 h before addition of further LiOH (313 mg, 7.5 mmol) and heating at reflux for an additional 2 h. Volatiles were then removed in vacuo, and the aqueous layer acidified to pH 3 with 1 M aq. HCl and extracted with EtOAc. The aqueous layer was concentrated in vacuo to a colourless oil which was purified on silica (Biotage Isolera, SNAP 50 g cartridge, 0.7 M NH$_3$ in MeOH/DCM, 4:1) to yield (3S)-3-{[1-(tert-butoxycarbonyl)piperidin-4-yl]amino}pentanoic acid (0.91 g) as a white powder, which was used crude in the next step.

LC/MS (method C): m/z 301 (M+H)+ (ES+), at 0.62 min, UV active.

Tert-butyl 4-{[(3S)-1-methoxy-1-oxopentan-3-yl]amino}piperidine-1-carboxylate (624 mg, assumed 0.9 mmol), 1-methyl-2-chloropyridinium iodide (584 mg, 2.3 mmol) and Et$_3$N (0.64 mL, 4.6 mmol) in MeCN (40 mL) were heated to reflux for 22 h. The mixture was purified on silica (Biotage isolera, SNAP 50 g cartridge, EtOAc/isohexane, 1;1 to 100% EtOAc over 5 CV and then 100% EtOAc over 10 CV) to yield tert-butyl 4-[(2S)-2-ethyl-4-oxoazetidin-1-yl]piperidine-1-carboxylate (194 mg, 80%) as a colourless oil.

LC/MS (method C): m/z 305 (M+Na)+ (ES+), at 1.26 min, UV active.

To tert-butyl 4-[(2S)-2-ethyl-4-oxoazetidin-1-yl]piperidine-1-carboxylate (194 mg, 0.7 mmol) in DCM (3 mL) was added TFA (3 mL) and the mixture stirred at rt for 30 min. The solvent was removed in vacuo to yield intermediate 8, (4S)-4-ethyl-1-(piperidin-4-yl)azetidin-2-one TFA salt (374 mg) as a brown oil, which was used crude in the next step. The data for the title compound are in table 2.

Route 3

Procedure for the Preparation of Intermediate 9, 4-(3,3-difluoroazetidin-1-yl)piperidine

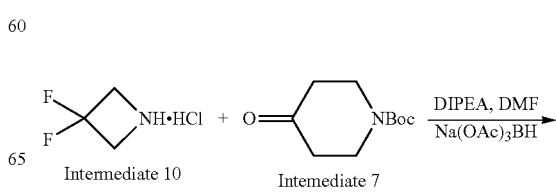

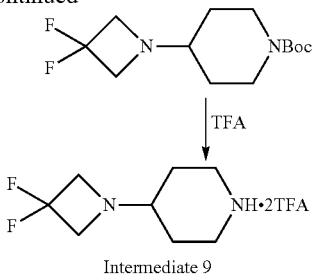

Intermediate 9

A solution of 3,3-difluoroazetidine hydrochloride (300 mg, 2.3 mmol), tert-butyl 4-oxopiperidine-1-carboxylate (461 mg, 2.3 mmol) and DIPEA (0.40 mL, 2.3 mmol) in DMF (6 mL) was heated to 50° C. for 16 h before cooling to rt, addition of sodium triacetoxyborohydride (1.23 g, 5.8 mmol) and AcOH (0.13 mL, 2.3 mmol) and further heating at 40° C. for 16 h. The mixture was cooled to rt, quenched by addition of sat. aq. NaHCO₃ (3 mL) and concentrated in vacuo. The residue was diluted with DCM (15 mL) and washed with sat. aq. NaHCO₃ (15 mL) and brine (15 mL). Organics were dried (Biotage phase separator) and concentrated in vacuo. The crude residue was purified on silica (Biotage Isolera, SNAP 25 g cartridge, 0-10% MeOH/DCM and subsequently SNAP 25 g cartridge, 0-5% MeOH/DCM) to yield tert-butyl 4-(3,3-difluoroazetidin-1-yl)piperidine-1-carboxylate (273 mg, 43%) as a white crystalline solid, which was used directly in the next step.

To tert-butyl 4-(3,3-difluoroazetidin-1-yl)piperidine-1-carboxylate (273 mg, 1.0 mmol) in DCM (8 mL) at 0° C. was added TFA (2 mL) and the mixture stirred at rt for 16 h. The reaction mixture was then concentrated in vacuo to yield intermediate 9, 4-(3,3-difluoroazetidin-1-yl)piperidine. 2TFA as a pink oil, which was used directly in the next step. The data for the title compound are in table 2.

Step 1: Alternative Work Up Procedure

The reaction was treated with H₂O(0.5 mL) and concentrated in vacuo. The crude residue was applied directly to a 25 g SNAP chromatography cartridge and eluted with a gradient 0-10% MeOH/DCM (Biotage Isolera).

Route 4

Procedure for the Preparation of Intermediate 15, 1-(piperidin-4-yl)azetidin-2-one.TFA Intermediate 15

To tert-butyl 4-oxopiperidine-1-carboxylate (5.0 g, 25.1 mmol) in MeOH (50 mL) was added methyl 3-aminopropanoate (3.5 g, 25.1 mmol) and Et₃N (10.7 mL, 75.3 mmol) and the reaction mixture stirred at 50° C. for 7 h. The mixture was then cooled to rt, followed by addition of NaBH₃CN (4.75 g, 75.1 mmol) portionwise and further stirring at rt for 17 h. The solvent was then removed in vacuo and the residue partitioned between H₂O (250 mL) and EtOAc (200 mL). The layers were separated and the aqueous layer extracted with EtOAc (2×200 mL). Combined organics were dried (Na₂SO₄), the solvent was removed in vacuo and the residue was purified by column chromatography (normal basic activated alumina, 10-13% EtOAc/hexane) to give tert-butyl 4-((3-methoxy-3-oxopropyl)amino)piperidine-1-carboxylate (3.30 g, 47%) as a yellow gum.

LC/MS (method A): m/z 287 (M+H)+ (ES+), at 3.82 min, UV active.

To a solution of tert-butyl 4-((3-methoxy-3-oxopropyl)amino) piperidine-1-carboxylate (2.0 g, 7.0 mmol) in THF (20 mL) was added methyl magnesium bromide (3.5 mL, 10.5 mmol) dropwise at 0° C., and the resulting mixture stirred at rt for 50 h. The reaction was quenched with sat. aq. NH₄Cl, the solvent removed in vacuo and the residue partitioned between H₂O (150 mL) and EtOAc (120 mL). The layers were separated and the aqueous layer further extracted with EtOAc (2×120 mL). Combined organics were dried (Na₂SO₄), the solvent removed in vacuo and the residue purified by column chromatography (normal basic activated alumina, 8-10% EtOAc/hexane) to give tert-butyl 4-(2-oxoazetidin-1-yl)piperidine-1-carboxylate (600 mg, 35%) as a yellow gum.

LC/MS (method B): m/z 255 (M+H)+ (ES+), at 3.63 min, UV active.

To tert-butyl 4-(2-oxoazetidin-1-yl) piperidine-1-carboxylate (600 mg, 2.4 mmol) in DCM (5 mL) at 0° C. was added trifluoroacetic acid (0.4 mL, 4.7 mmol) dropwise and the resulting mixture stirred at rt for 8 h. The solvent was then removed in vacuo and the residue purified by trituration with ether (3×2 mL) to give Intermediate 15, 1-(piperidin-4-yl) azetidin-2-one.TFA (510 mg, 81%) as a yellow gum. The data for the title compound are in table 2.

General Synthetic Procedures for Examples

Route a

Typical Procedure for the Preparation of Piperidines Via Reductive Amination, as Exemplified by the Preparation of Example 1-1 Ethyl 2-[4-(3,3-difluoroazetidin-1-yl)piperidin-1-yl]-6-azaspiro[3.4]octane-6-carboxylate Intermediate 9

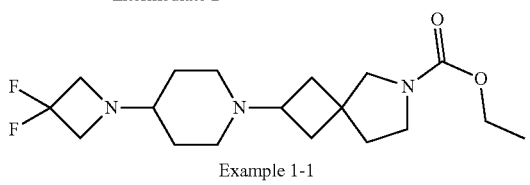

Intermediate 2

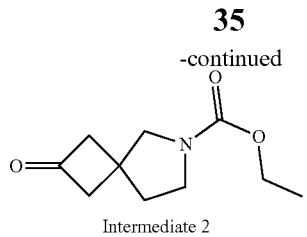

Example 1-1

A solution of crude 4-(3,3-difluoroazetidin-1-yl)piperidine (assumed 1.0 mmol), ethyl 2-oxo-6-azaspiro[3.4]octane-6-carboxylate (183 mg, 0.9 mmol) and DIPEA (0.34 mL, 2.0 mmol) in DMF (6 mL) was stirred at 40° C. for 2 h. The solution was cooled to rt before addition of sodium triacetoxyborohydride (522 mg, 2.5 mmol) and AcOH (60 µL, 1.0 mmol) and further stirring at 40° C. for 16 h. The solvent was removed in vacuo and the residue diluted with sat. aq. NaHCO₃ (15 mL) and extracted with DCM (2×15 mL). Combined organics were dried (Biotage phase separator cartridge) and concentrated in vacuo. The crude residue was purified on silica (Biotage Isolera, SNAP 25 g cartridge, 0-10% MeOH/DCM) and subsequently by prep HPLC [reverse phase (Gemini-NX, C18, 5µ, 100×30 mm), 30 mL per min, gradient 30% (0.3 min), then 30-60% (over 8.7 min), then 60% (for 0.5 min), then 60-100% (over 0.2 min), then 100% (for 1 min), then 30% (for 0.8 min), MeCN/0.2% NH₃ in water] to yield ethyl 2-[4-(3,3-difluoroazetidin-1-yl)piperidin-1-yl]-6-azaspiro[3.4]octane-6-carboxylate isomer 1 (29 mg, 9%) as a colourless oil and Example 1-1, ethyl 2-[4-(3,3-difluoroazetidin-1-yl)piperidin-1-yl]-6-azaspiro[3.4]octane-6-carboxylate isomer 2 (30 mg, 9%) as a colourless oil. The data for the title compound are in table 3

Route a Alternative Work Up Procedure

The reaction was allowed to cool to rt, treated with H₂O (0.5 mL) and concentrated in vacuo.

The crude residue was applied directly to a 10 g SNAP chromatography cartridge and eluted with a gradient 0-10% MeOH/DCM (Biotage Isolera). Relevant fractions were combined and further purified by reverse phase prep HPLC.

Route b

Typical Procedure for the Preparation of Piperidines Via Reductive Amination, as Exemplified by the Preparation of Example 1-3 ethyl 2-[4-(2-oxoazetidin-1-yl)piperidin-1-yl]-6-azaspiro[3.4]octane-6-carboxylate

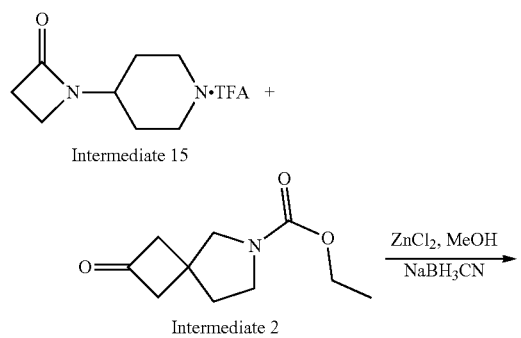

Intermediate 15

Intermediate 2

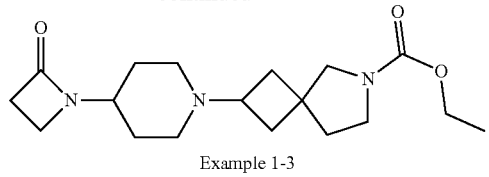

Example 1-3

A solution of 1-(piperidin-4-yl) azetidin-2-one.TFA (200 mg, 0.8 mmol), ethyl 2-oxo-6-azaspiro [3.4]octane-6-carboxylate (254 mg, 1.3 mmol) and Et₃N (0.6 mL, 3.9 mmol) in MeOH (10 mL) was stirred at 55° C. for 5 h. The reaction mixture was then cooled to 0° C. before addition of NaBH₃CN (246 mg, 3.9 mmol) portionwise and further stirring at 25° C. for 17 h. The solvent was removed in vacuo, the residue partitioned between H₂O (100 mL) and DCM (80 mL) and the layers separated. The aqueous layer was extracted with DCM (2×80 mL) and combined organics dried (Na₂SO₄) and the solvent removed in vacuo. The residue was purified by prep HPLC [reverse phase (X-BRIDGE C-18, 150×9 mm, 5 µm), 17 mL per min, gradient 20% (over 30.0 min), 100% (over 2.0 min), then 20% (over 2.0 min), 0.1% NH₃ in MeCN/water] to give ethyl 2-(4-(2-oxoazetidin-1-yl)piperidin-1-yl)-6-azaspiro [3.4]octane-6-carboxylate isomer-1 (45 mg, 18%) as a yellow gum and Example 1-3, ethyl 2-(4-(2-oxoazetidin-1-yl) piperidin-1-yl)-6-azaspiro[3.4]octane-6-carboxylate isomer-2 (28 mg, 11%) as a yellow gum. The data for the title compound are in table 3.

Route c

Typical Procedure for the Preparation of Piperidines Via Reductive Amination, as Exemplified by the Preparation of Example 1-5, ethyl 2-{4-[(2S)-2-ethyl-4-oxoazetidin-1-yl]piperidin-1-yl}-6-azaspiro [3.4]octane-6-carboxylate

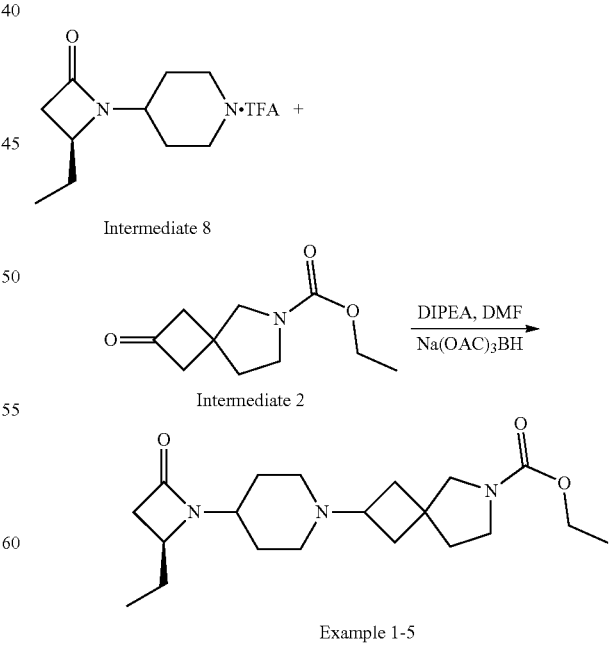

Example 1-5

To crude(4S)-4-ethyl-1-(piperidin-4-yl)azetidin-2-one TFA salt (374 mg, assume 0.7 mmol) in DMF (5 mL) was added DIPEA (0.60 mL, 3.4 mmol), AcOH (60 µL, 1.1 mmol), ethyl 2-oxo-6-azaspiro[3.4]octane-6-carboxylate (136 mg, 0.7 mmol) and sodium triacetoxyborohydride (437 mg, 2.1 mmol) and the mixture stirred at rt for 65 h. The reaction mixture was concentrated to remove DMF and the residue purified on silica (Biotage Isolera, SNAP 25 cartridge, 0-10% 0.7 $NH_3$ in MOH/DCM over 10 CV) to yield a mixture of two isomers as a yellow residue. This was further purified by prep HPLC [reverse phase (Gemini-NX, 18, 5µ, 100×30 mm), 30 mL per min, gradient 30%(0.3 min), then 30-60% (over 8.7 min), then 60% (for 0.5 min), then 60-100% (over 0.2 min), then 100% (for 1 min), then 30% (for 0.8 min), MeCN/0.2% $NH_3$ in water] to yield ethyl 2-4-[(2S)-2-ethyl-4-oxoazetidin-1-yl]piperidin-1-yl-6-azaspiro[3.4]octane-6-carboxylate isomer (100 mg, 40%) as a gum and Example 1-5, ethyl 2-{4-[(2S)-2-ethyl-4-oxoazetidin-1-yl]}piperidin-1-yl-6-azaspiro[3.4]octane-6-carboxylate isomer 2 (76 mg, 30%) a gum. The data for the title compound are in table 3.

TABLE 2

| | | Characterising data and commercial sources for starting materials and intermediates | |
|---|---|---|---|
| Intermediate | Route | Name | Data |
| 1 | | 6-Boc-2-oxo-6-azaspiro[3.4]octane | Commercially available, CAS: 203661-71-6 |
| 2 | Route 1 and intermediates 1 and 5 | Ethyl 2-oxo-6-azaspiro[3.4]octane-6-carboxylate | $^1$H NMR: (400 MHz, $CDCl_3$) δ: 1.27 (t, J = 7.0 Hz, 3H), 2.08 (t, J = 6.2 Hz, 2 H), 2.94-3.17 (m, 4 H), 3.49-3.59 (m, 4 H), 4.15 (q, J = 7.0 Hz, 2 H) |
| 3 | Route 1 and intermediates 1 and 4 | Methyl 2-oxo-6-azaspiro[3.4]octane-6-carboxylate | $^1$H NMR: (400 MHz, $CD_3OD$) δ:: 2.06-2.15 (m, 2 H), 2.94 - 3.04 (m, 2 H), 3.05-3.17 (m, 2 H), 3.47 (td, J = 6.8, 2.5 Hz, 2 H), 3.54 (d, J = 2.5 Hz, 2 H), 3.69 (s, 3 H) |
| 4 | | Methyl chloroformate | Commercially available, CAS: 79-22-1 |
| 5 | | Ethyl chloroformate | Commercially available, CAS: 541-41-3 |
| 6 | | (3S)-3-Aminopentanoic acid | Commercially available. CAS: 14389-77-6 |
| 7 | | Tert-butyl 4-oxopiperidine-1-carboxylate | Commercially available. CAS: 79099-07-3 |
| 8 | Route 2 and intermediates 6 and 7 | (4S)-4-Ethyl-1-(piperidin-4-yl)azetidin-2-one.TFA | m/z 183 (M + H)+ (ES+) |
| 9 | Route 3 and intermediates 7 and 10 | 4-(3,3-Difluoroazetidin-1-yl)piperidine. 2TFA | $R_f$ = 0.10 (MeOH/DCM, 1:9) |
| 10 | | 3,3-Difluoroazetidine hydrochloride | Commercially available. CAS: 288315-03-7 |
| 11 | | (R)-Methyl-2-azetidine carboxylate.HCl | Commercially available CAS: 647854-63-5 |
| 12 | Route 3 with step 2 HCl instead of TFA. Intermediates 7 and 11 | Methyl (2R)-1-(piperidin-4-yl)azetidine-2-carboxylate.2HCl | $R_f$ = 0 (MeOH/DCM, 1:9) |
| 13 | | Methyl β-alaninate | Commercially available. CAS: 4138-35-6 |
| 14 | | MeMgBr | Commercially available. CAS: 75-16-1 |
| 15 | Route 4 and intermediates 7 and 13 | 1-(piperidin-4-yl)azetidin-2-one.TFA | (LC/MS method A) m/z 155 (M + H)$^+$ (ES$^+$) at 1.87 min, UV active |
| 16 | Route 2 and intermediates 7 and 17 | (4R)-4-Ethyl-1-(piperidin-4-yl)azetidin-2-one.TFA | (LC/MS method D) m/z 183 (M + H)$^+$ (ES$^+$) at 1.29 min, UV active |
| 17 | | (3R)-3-Aminopentanoic acid | Commercially available. CAS: 131347-76-7 |
| 18 | Route 2 and intermediates 7 and 19 | (4R)-4-methyl-1-(piperidin-4-yl)azetidin-2-one | m/z 169 (M + H)$^+$ (ES$^+$) |
| 19 | | (3R)-3-aminobutanoic acid | Commercially available. CAS: 3775-73-3 |
| 20 | Route 2 and intermediates 7 and 21 | (4S)-4-methyl-1-(piperidin-4-yl)azetidin-2-one | m/z 169 (M + H)$^+$ (ES$^+$) |
| 21 | | (3S)-3-aminobutanoic acid | Commercially available. CAS: 3775-72-2 |

TABLE 3

| Ex. No. | Name | Intermediate | Synthetic method | $^1$H NMR | LCMS Method | LCMS data |
|---|---|---|---|---|---|---|
| 1-1 | Isomer 2: Ethyl 2-[4-(3,3-difluoroazetidin-1-yl)piperidin-1-yl]-6-azaspiro[3.4]octane-6-carboxylate | 2 and 9 | Route a | (400 MHz, DMSO-d$_6$) δ: 1.13 (t, J = 7.0 Hz, 3 H), 1.57-1.60 (m, 2 H), 1.70-1.82 (m, 6 H), 1.91-1.96 (m, 2 H), 2.53-2.64 (m, 3 H), 2.03-2.14 (m, 1 H), 3.10-3.26 (m, 6 H), 3.48 (t, J = 12.5 Hz, 4 H), 3.96 (q, J = 7.0 Hz, 2 H) | E | m/z 358 (M + H)$^+$ (ES$^+$) at 3.20 min, UV inactive |
| 1-2 | Isomer 2: Ethyl 2-{4-[(2R)-2-(methoxycarbonyl)azetidin-1-yl]piperidin-1-yl}-6-azaspiro[3.4]octane-6-carboxylate | 2 and 12 | Route a with alternative work up procedure | (400 MHz, DMSO-d$_6$) δ: 0.99-1.15 (m, 5 H), 1.47-2.14 (m, 13 H), 2.53-2.65 (m, 2 H), 2.81 (q, J = 8.0 Hz, 1 H), 3.11-3.27 (m, 6 H), 3.58 (s, 3 H), 3.67 (t, J = 8.0 Hz, 1 H), 3.97 (q, J = 7.0 Hz, 2 H) | E | m/z 380 (M + H)$^+$ (ES$^+$) at 5.41 min, UV active |
| 1-3 | Isomer 2: Ethyl 2-[4-(2-oxoazetidin-1-yl)piperidin-1-yl]-6-azaspiro[3.4]octane-6-carboxylate | 2 and 15 | Route b | (400 MHz, CDCl$_3$) δ: 1.22-1.30 (m, 3 H), 1.66-2.54 (m, 12 H), 2.66-3.03 (m, 5 H), 3.21-3.68 (m, 7 H), 4.08-4.19 (m, 2 H) | A | m/z 336 (M + H)$^+$ (ES$^+$) at 3.30 min, UV active |
| 1-4 | Isomer 2: Ethyl 2-{4-[(2S)-2-methyl-4-oxoazetidin-1-yl]piperidin-1-yl}-6-azaspiro[3.4]octane-6-carboxylate | 2 and 20 | Route c | (400 MHz, CDCl$_3$) δ: 1.19-1.22 (m, 3 H), 1.33 (d, J = 6.0 Hz, 3 H), 1.56-1.91 (m, 10 H), 1.97-2.07 (m, 2 H), 2.41 (dd, J = 14.5, 2.0 Hz, 1 H), 2.57-2.69 (m, 1 H), 2.76-2.90 (m, 2 H), 2.97 (dd, J = 14.5, 5.0 Hz, 1 H), 3.23 (d, J = 20.5 Hz, 2 H), 3.35 (dt, J = 20.0, 6.5 Hz, 2 H), 3.46-3.58 (m, 1 H), 3.68-3.75 (m, 1 H), 4.07 (q, J = 7.0 Hz, 2 H) | E | m/z 350 (M + H)$^+$ (ES$^+$) at 3.38 min, UV active |
| 1-5 | Isomer 2: Ethyl 2-{4-[(2S)-2-ethyl-4-oxoazetidin-1-yl]piperidin-1-yl}-6-azaspiro[3.4]octane-6-carboxylate | 2 and 8 | Route c | (400 MHz, CDCl$_3$) δ: 0.89 (t, J = 7.0 Hz, 3 H), 1.24 (t, J = 6.5 Hz, 3 H), 1.39-1.50 (m, 1 H), 1.55 -2.16 (m, 13 H), 2.48 (d, J = 7.0 Hz, 1 H), 2.56-2.71 (m, 1 H), 2.76-2.94 (m, 3 H), 3.24-3.43 (m, 4 H), 3.48-3.64 (m, 2 H), 4.10 (q, J = 7.0 Hz, 2 H) | E | m/z 364 (M + H)$^+$ (ES$^+$) at 3.77 min, UV active |
| 1-6 | Isomer 2: Ethyl 2-{4-[(2R)-2-methyl-4-oxoazetidin-1-yl]piperidin-1-yl}-6-azaspiro[3.4]octane-6-carboxylate | 2 and 18 | Route c | (400 MHz, CDCl$_3$) δ: 1.20-1.25 (m, 3 H), 1.34 (d, J = 6.0 Hz, 3 H), 1.57-2.09 (m, 10 H), 2.30-3.59 (m, 12 H), 3.66-3.77 (m, 1 H), 4.05-4.17 (m, 2 H) | E | m/z 350 (M + H)$^+$ (ES$^+$) at 3.38 min, UV active |
| 1-7 | Isomer 2: Ethyl 2-{4-[(2R)-2-ethyl-4-oxoazetidin-1-yl]piperidin-1-yl}-6-azaspiro[3.4]octane-6-carboxylate | 2 and 16 | Route c | (400 MHz, CDCl$_3$) δ: 0.85-0.92 (m, 3 H), 1.19-1.25 (m, 3 H), 1.37-1.48 (m, 1 H), 1.56-2.07 (m, 11 H), 2.43-3.55 (m, 13 H), 4.05-4.17 (m, 2 H) | E | m/z 364 (M + H)$^+$ (ES$^+$) at 3.73 min, UV active |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen*, 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader.

$pEC_{50}$ and $E_{max}$ figures were calculated from the resulting data for each receptor subtype.

The results are set out in Table 4 below.

For each example with the 4-5 spiro system two diastereomers exist which have been separated, unless stated otherwise, and assigned based on their retention time on LCMS analytical trace. In most examples, isomer 1 is not active. Analytical data for active isomers is reported in Table 3. Data for several weakly active compounds are included in Table 4 to highlight preference of absolute stereochemistry.

TABLE 4

| | Muscarinic Activity | | | |
|---|---|---|---|---|
| Ex. No. | $pEC_{50}$ $M_1$ (% Emax cf. ACh) | $pEC_{50}$ $M_2$ (% Emax cf. ACh) | $pEC_{50}$ $M_3$ (% Emax cf. ACh) | $pEC_{50}$ $M_4$ (% Emax cf. ACh) |
| ACh | 8.3 (102) | 7.8 (105) | 8.1 (115) | 8.1 (110) |
| 1-1 Isomer 2 | 6.0 (24) | NT | NT | 6.8 (26) |
| 1-2 Isomer 2 | <4.7 (37) | <4.7 (7) | <4.7 (7) | 7.2 (67) |
| 1-3 Isomer 2 | <4.7 (20) | NT | NT | 6.7 (23) |
| 1-4 Isomer 2 | <4.7 (18) | NT | NT | 6.8 (41) |
| 1-5 Isomer 2 | 6.5 (69) | <4.7 (37) | <4.7 (0) | 7.0 (56) |
| 1-6 Isomer 2 | <4.7 (13) | NT | NT | 6.6 (74) |
| 1-7 Isomer 2 | 6.1 (94) | *6.3 (26) | <4.7 (21) | 7.1 (101) |

*-variable results,
NT - Not tested

Example B

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and optionally 1% by weight of magnesium stearate and filling the resulting mixture into standard opaque hard gelatin capsules.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for the treatment of Alzheimer's Disease, dementia with Lewy bodies or schizophrenia in a subject, comprising administering to the subject an effective amount of a compound of the formula (1):

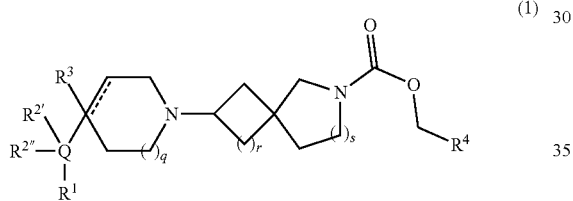

or a salt thereof, wherein
q is 1;
r is 1 or 2;
s is 0 or 1 where the total of r and s is 1 or 2;
Q is an azetidine linked to the adjacent six-membered ring by the nitrogen atom of the azetidine ring;
$R^1$ is selected from hydrogen; methyl; ethyl; fluorine oxo; and COOMe;
$R^{2'}$ and $R^{2''}$ are independently selected from hydrogen; fluorine; and a $C_{1-6}$ non-aromatic hydrocarbon group;
$R^3$ is hydrogen;
$R^4$ is hydrogen or a $C_{1-6}$ non-aromatic hydrocarbon group which is optionally substituted with one to six fluorine atoms and
the dotted line indicates a single bond.

2. The method according to claim 1, wherein $R^4$ is selected from hydrogen and methyl.

3. The method according to claim 1, wherein the compound is selected from the group consisting of:
Ethyl 2-[4-(3,3-difluoroazetidin-1-yl)piperidin-1-yl]-6-azaspiro[3.4]octane-6-carboxylate;
Ethyl 2-{4-[(2R)-2-(methoxycarbonyl)azetidin-1-yl]piperidin-1-yl}-6-azaspiro[3.4]octane-6-carboxylate;
Ethyl 2-[4-(2-oxoazetidin-1-yl)piperidin-1-yl]-6-azaspiro[3.4]octane-6-carboxylate;
Ethyl 2-{4-[(2S)-2-methyl-4-oxoazetidin-1-yl]piperidin-1-yl}-6-azaspiro[3.4]octane-6-carboxylate;
Ethyl 2-{4-[(2S)-2-ethyl-4-oxoazetidin-1-yl]piperidin-1-yl}-6-azaspiro[3.4]octane-6-carboxylate;
Ethyl 2-{4-[(2R)-2-methyl-4-oxoazetidin-1-yl]piperidin-1-yl}-6-azaspiro[3.4]octane-6-carboxylate;
Ethyl 2-{4-[(2R)-2-ethyl-4-oxoazetidin-1-yl]piperidin-1-yl}-6-azaspiro[3.4]octane-6-carboxylate;
or a salt thereof.

4. The method according to claim 1, wherein the compound is a pharmaceutically acceptable salt of a compound as defined in claim 1.

5. The method according to claim 1, wherein the compound is administered to the subject as in the form of a pharmaceutical composition comprising the compound as defined in claim 1 and a pharmaceutically acceptable excipient.

6. The method according to claim 1 wherein the moiety:

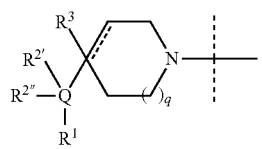

is selected from:

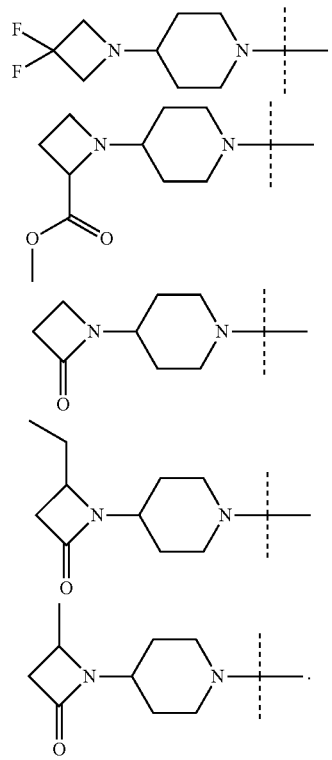

7. The method according to claim 1 wherein the moiety:

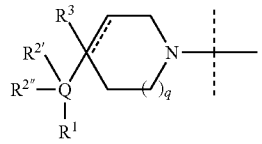

is selected from:
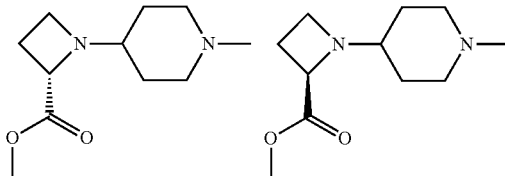
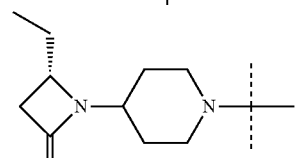
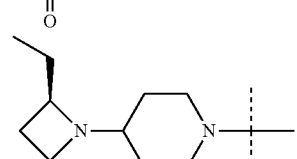
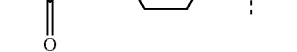
and
8. The method according to claim 1, wherein the disorder is Alzheimer's Disease.
9. The method according to claim 1, wherein the disorder is dementia with Lewy bodies.
10. The method according to claim 1, wherein the disorder is schizophrenia.
* * * * *